United States Patent [19]

Massy

[11] 4,291,162

[45] Sep. 22, 1981

[54] AMINOTRIAZINEPOLYCARBOXYLIC ACIDS AND PARTIAL ESTERS THEREOF

[75] Inventor: Derek J. R. Massy, Linton, England

[73] Assignee: Ciba-Geigy Corporation, Ardsley, N.Y.

[21] Appl. No.: 169,063

[22] Filed: Jul. 15, 1980

[30] Foreign Application Priority Data

Jul. 25, 1979 [GB] United Kingdom ............ 25963/79

[51] Int. Cl.$^3$ ................. C07D 251/70; C07D 251/48
[52] U.S. Cl. .................................. 544/199; 544/198; 544/205; 544/206; 544/207
[58] Field of Search ............... 544/198, 199, 205, 206, 544/207

[56] References Cited

U.S. PATENT DOCUMENTS

| | | | |
|---|---|---|---|
| 2,266,747 | 12/1941 | Engelmann et al. | 260/205 |
| 2,337,220 | 12/1943 | Albrecht et al. | 260/401 |
| 2,494,966 | 1/1950 | Sallmann | 260/401 |
| 2,763,649 | 9/1956 | Albrecht et al. | 260/249.6 |
| 3,530,086 | 9/1970 | Porret et al. | 260/30.2 |
| 3,697,520 | 10/1972 | Winter | 260/249.6 |

FOREIGN PATENT DOCUMENTS 1019338  2/1966  United Kingdom .
1195087  6/1970  United Kingdom .

Primary Examiner—John M. Ford
Attorney, Agent, or Firm—Harry Falber

[57] ABSTRACT

New compounds of formula

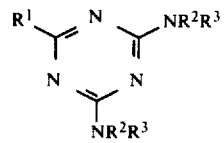

where $R^1$ represents —$NR^2R^3$, an alkyl group, a mononuclear aryl group, a phenylalkylene group, or a group of formula

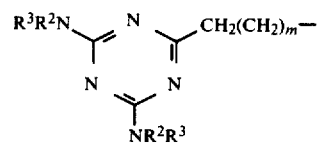

$R^2$ and $R^3$ each represent —H, —$CHR^4OR^5$, —$CHR^4$—S—$R^6$—COOQ, or

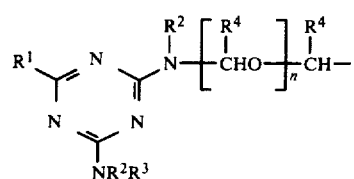

$R^2$ and $R^3$ in formulae I and III being such that at most one represents a group of formula III and at least two each represent a group —$CHR^4$—S—$R^6$—COOQ, $R^4$ and $R^5$ represent —H or alkyl groups, $R^6$ is an alkylene group, optionally substituted by a carboxyl group, at least two Q in formula I represent —H and the remainder may alternatively represent alkyl groups, m is 1, 2, or 3, and n is zero or 1, e.g., hexakis(N-2-carboxyethylthiomethyl)melamine, a tris(N-2-carboxyethylthiomethyl)tris(N-2-(butoxymethyl)melamine, or tetrakis(N-2-carboxyethylthiomethyl)acetoguanamine, are useful as curing agents for epoxide resins.

9 Claims, No Drawings

AMINOTRIAZINEPOLYCARBOXYLIC ACIDS AND PARTIAL ESTERS THEREOF

BACKGROUND OF THE INVENTION

This invention relates to new aminotriazinepolycarboxylic acids and partial esters thereof, to their preparation, and to their use as curing agents for epoxide resins.

U.S. Pat. No. 2,337,220 disclosed the reaction of mercaptans, especially aliphatic mercaptocarboxylic acids, with N-methylol or N-halomethyl derivatives of amides. Reaction between thioglycolic acid and an N-methylolamide is said to result in formation of an N-(carboxymethylthiomethyl)amide, i.e., etherification, and not esterification, occurs. The detailed disclosures are restricted to the use of N-hydroxymethylamides of aliphatic monocarboxylic acids containing at least 12 carbon atoms, but amides of many other kinds of acids and also urea, thiourea, and melamine, as well as their substitution products, are cited as possible reactants.

U.S. Pat. No. 2,763,649 described the formation of hardenable, ternary condensation products by reaction of (a) a formaldehyde condensation product of a compound of the aminotriazine or urea group or an ether thereof with an alcohol of low molecular weight, (b) an aliphatic compound which contains a carbon chain of at least 7 carbon atoms and a reactive hydrogen atom bound to a heteroatom, and (c) a hydroxy- or mercapto - carboxylic acid or a hydroxy- or mercapto-sulfonic acid. When (a) is a methylolated aminotriazine or an ether thereof, 1 mol. of (c) is employed per mol. of (a).

Neither of these references discloses the production of aminotriazinepolycarboxylic acids.

We have found that reaction of an aminotriazine containing at least two N-methylol or N-alkoxymethyl groups with at least two equivalents of a mercaptocarboxylic acid gives aminotriazinepolycarboxylic acids in which the carboxyl groups are linked to the aminotriazine ring through thioether linkages. Further, when a poly(alkoxymethylamino)triazine is used as starting material, a subsequent esterification may also occur to a minor extent, so that the product may contain not only the aminotriazinepolycarboxylic acid but also its partial esters, where the esterifying group is the same as the original etherifying group; thus, with methoxymethylaminotriazines, methyl esters of the polycarboxylic acids may be also formed. We have also found that partial esters can be obtained by replacing a proportion of the mercaptocarboxylic acid by an ester thereof, or by partial reaction of the aminotriazinepolycarboxylic acid with an alcohol.

Polycarboxylic acids are well known as curing agents for epoxide resins, i.e., substances having more than one 1,2-epoxide group per average molecule. These known acids often require a high temperature and/or extended heating in order fully to cure the resin. We have further found that the new polycarboxylic acids, and partial esters thereof which contain at least two carboxylic acid groups, cure epoxide resins on heating at moderate temperatures and for only a short period.

SUMMARY OF THE INVENTION

Accordingly, one aspect of this invention provides aminotriazinepolycarboxylic acids, and partial esters thereof which contain at least two free carboxylic acid groups, having the general formula

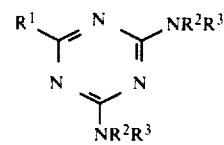

where
R$^1$ represents a group of formula —NR$^2$R$^3$, a straight chain or branched alkyl group of from 1 to 17 carbon atoms, a mononuclear aryl group of 6 to 10 carbon atoms, a phenylalkylene group wherein the alkylene moiety has from 1 to 4 carbon atoms, or a group of formula

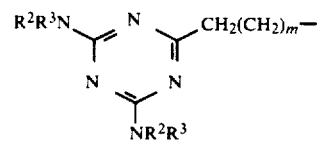

R$^2$ and R$^3$ may be the same or different and each represents a hydrogen atom, a group of formula —CHR$^4$OR$^5$, a group of formula —CHR$^4$—S—R$^6$—COOQ, or a group of formula

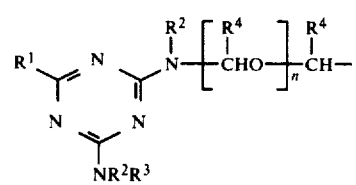

R$^2$ and R$^3$ in formulae I and III being selected such that at most one of them represents a group of formula III and at least two of them each represent a group of formula —CHR$^4$—S—R$^6$—COOQ, m represents an integer of from 1 to 3, each R$^4$ represents a hydrogen atom or a straight chain or branched alkyl group of from 1 to 3 carbon atoms, each R$^5$ represents a hydrogen atom or a straight chain or branched alkyl group of from 1 to 8, and preferably 1 to 4, carbon atoms, each R$^6$ represents a divalent straight chain or branched alkylene group of from 1 to 4 carbon atoms, which may be substituted by a further group —COOQ, each Q represents a hydrogen atom or a straight chain or branched alkyl group of from 1 to 8 carbon atoms, such that on average at least two Q in formula I each represent a hydrogen atom, and n represents zero or 1.

As indicated above, one (but not more than one) of the various symbols R$^2$ and R$^3$ in formula I may represent a triazine ring of formula III. A symbol R$^2$ or R$^3$ in this ring may represent yet another ring of formula III, and in this way a chain of substituted triazine rings linked by alkylene or alkylene ether bridges may be formed. For ease of making the new compounds, and for best results in curing epoxide resins, acids and esters of formula I preferably have a molecular weight of at most 2000.

DESCRIPTION OF THE PREFERRED EMBODIMENTS

The group $R^1$ is preferably a group $-NR^2R^3$, where $R^2$ and $R^3$ are as hereinbefore defined, but it may also, for example, be a heptadecyl, nonyl, propyl, or benzyl group, and particularly a methyl, phenyl, or undecyl group.

The symbols $R^4$ all each preferably represent a hydrogen atom. At least one of Q and at least one of $R^5$ preferably represents an alkyl group, such as a methyl, n-butyl, isobutyl, or 2-ethylhexyl group. All the groups $R^6$ in formula I preferably each represent a methylene, ethylene, or 2-carboxyethylidene group.

The further preferred substances of formula I are the acids and esters which are also substantially of the formula

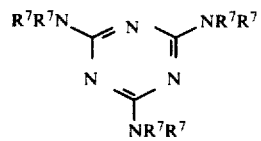
IV where from two to six of $R^7$ each denote a group of formula $-CH_2SCH_2COOQ$, $-CH_2SCH_2CH_2COOQ$, $-CH_2SCH(COOQ)CH_2COOQ$, or $-CH_2SCH(CH_3)COOQ$, where Q has the meaning previously assigned, the remaining $R^7$, if any, each denoting a hydrogen atom, and those which are also substantially of the formula

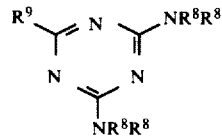
V where
from two to four of $R^8$ each denote a group of formula $-CH_2SCH_2COOQ$, $-CH_2SCH_2CH_2COOQ$, $-CH_2SCH(COOQ)CH_2COOQ$, or $-CH_2SCH(CH_3)COOQ$, where Q has the meaning previously assigned, the remaining $R^8$, if any, each denoting a hydrogen atom, and $R^9$ denotes a methyl, phenyl, or undecyl group.

Specific examples of acids of formula I are - hexakis(N-2-carboxyethylthiomethyl)melamine, hexakis(N-carboxymethylthiomethyl)melamine, tetrakis(N-2-carboxyethylthiomethyl)acetoguanamine, tetrakis(N-2-carboxyethylthiomethyl)benzoguanamine, and tetrakis(N-2-carboxyethylthiomethyl)lauroguanamine.

The acids or partial esters of formula I may be prepared by the reaction of at least 2 molar equivalents of a mercaptocarboxylic acid of the general formula $$HS-R^6-COOH \qquad VI$$

with one molar equivalent of the condensation product, which may if desired be alkylated, of an aminotriazine with an aldehyde, and having the general formula

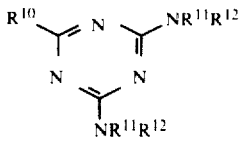
VII where
$R^6$ is as hereinbefore defined,
$R^{10}$ represents a group $-NR^{11}R^{12}$, or a straight chain or branched alkyl group of from 1 to 17 carbon atoms, a mononuclear aryl group of 6 to 10 carbon atoms, a phenylalkylene group wherein the alkylene moiety has from 1 to 4 carbon atoms, or a group of the formula

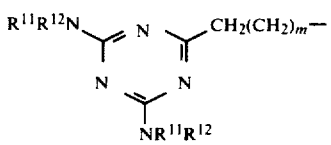
VIII and $R^{11}$ and $R^{12}$ may be the same or different and each represents a hydrogen atom, a group $-CHR^4-O-R^5$, or a group of formula

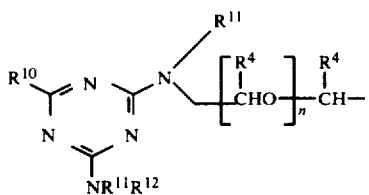
IX where $R^4$, $R^5$, m, and n are as hereinbefore defined, $R^{11}$ and $R^{12}$ in the compound of formula VII being selected such that at most one of them represents a group of formula IX and at least two of them each represent a group of formula $-CHR^4-OR^5$.

This reaction may be effected by mixing the components at room temperature or, preferably, an elevated temperature, usually between 50° and 150° C., either in the absence of a solvent or in the presence of a suitable solvent, such as water, methanol, ethanol, dioxan, acetone, glacial acetic acid, benzene or toluene, and, if desired, in the presence of an acid catalyst such as sulfuric or hydrochloric acid.

When, in formula VII, at least one of $R^{11}$ and $R^{12}$ represents a group of formula $-CHR^4-O-R^5$, where $R^5$ represents an alkyl group as aforesaid, the product is usually a mixture of the acid of formula I, in which Q represents a hydrogen atom, and a minor amount of the ester of formula I in which Q represents an identical alkyl group $R^5$, preferably a methyl, n-butyl, isobutyl, or 2-ethylhexyl group. Such mixtures may if desired be separated by conventional means, but usually they may be employed as curing agents for epoxide resins without such separation. The use of partial esters is often advantageous, e.g., if a cured epoxide resin of greater flexibility is required than would be obtained if the curing agent were solely an unesterified polycarboxylic acid of this invention.

According to a modification of the above process of this invention, to obtain a partial ester of formula I, an ester of formula

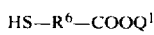   X where
R[6] is as hereinbefore defined and
Q[1] denotes a straight chain or branched alkyl group of 1 to 8 carbon atoms, e.g., a methyl, n-butyl, isobutyl, or 2-ethylhexyl group, is also employed as one of the reaction components.

This modification may be used as an alternative to the use of an alkylated aminotriazine-aldehyde condensation product (i.e., a compound of formula V where at least one of R[11] and R[12] represents a group of formula —CHR[4]—O—R[5], where R[5] represents an alkyl group as aforesaid), or it may be used, when such an alkylated condensation product is employed, to enhance the content of ester groups (which may be the same as, or different from, the ester groups formed by reaction with the liberated alcohol).

In a further method of preparing the partial esters of this invention, the aminotriazinepolycarboxylic acids of formula I, where at least three of the Q each represent a hydrogen atom, are esterified by conventional means employing an alcohol of formula

   XI where Q[1] has the meaning assigned above.

Of course, the proportion of an ester of formula X or an alcohol of formula XI should not be so great that the product contains on average less than two free carboxylic acid groups per molecule, otherwise the product will not be useful as a curing agent for epoxide resins.

In another method of making acids and partial esters of formula I, at least two molar equivalents of a mercaptocarboxylic acid of formula VI and, if required, an appropriate amount of an ester of formula X, are reacted with one molar equivalent of an aminotriazine of formula

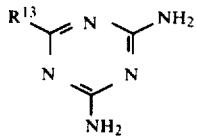   XII and at least two molar equivalents of an aldehyde of formula

R[4]CHO   XIII where
R[13] represents an unsubstituted amino group, a straight chain or branched alkyl group of from 1 to 17 carbon atoms, a mono- nuclear aryl group of 6 to 10 carbon atoms, a phenylalkylene group wherein the alkylene moiety has from 1 to 4 carbon atoms, or a group of formula

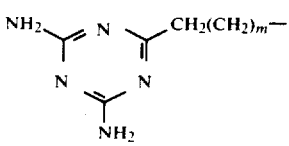   XIV and m and R[4] are as hereinbefore defined.

Preferably this reaction is carried out under aqueous conditions, the acid of formula IV, the ester of formula X (if used), and the aminotriazine of formula XII being kept in contact, optionally with heating, until they dissolve due to formation of the salt, and then the aldehyde of formula XIII is added. The mixture is then stirred until reaction is substantially complete. The reaction may be effected at room temperature, but preferably the reactants are heated at a temperature of from 50° to 100° C.

In a variation of the above method, using the same molar proportions, the acid of formula VI (and the ester of formula X, if used), may first be mixed with the aldehyde of formula XIII under aqueous or anhydrous conditions, and then the aminotriazine of formula XII is added. This reaction may also be effected at ambient or elevated temperature, and preferably the reactants are heated at a temperature of from 50° to 100° C.

In one particularly preferred embodiment of this invention, melamine is reacted, in the absence of any ester of formula X, with from 2 to 6 molar equivalents of thioglycolic, 2-mercaptopropionic, 3-mercaptopropionic acid, or mercaptosuccinic acid, and from 2 to 6 molar equivalents of formaldehyde, there being used the same number of equivalents of formaldehyde as of the mercaptoacid. In another particularly preferred embodiment, acetoguanamine, benzoguanamine, or lauroguanamine is reacted, in the absence of any ester of formula X, with from 2 to 4 molar equivalents of thioglycolic, 2-mercaptopropionic, 3-mercaptopropionic acid, or mercaptosuccinic acid, there being used the same number of equivalents of formaldehyde as of the mercaptoacid.

The aminotriazinepolycarboxylic acids of formula I in which all the R[4] and Q each represent a hydrogen atom may also be prepared by the reaction of one molar equivalent of an aminotriazine of the general formula

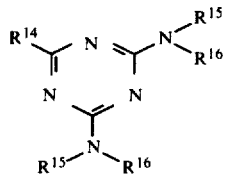   XV with at least two molar equivalents of a mercaptocarboxylic acid of formula VI aforesaid,
where
R[14] denotes a group of formula —NR[15]R[16], a straight chain or branched alkyl group of from 1 to 17 carbon atoms, a mononuclear aryl group of 6 to 10 carbon atoms, a phenylalkylene group wherein the alkylene moiety has from 1 to 4 carbon atoms, or a group of formula

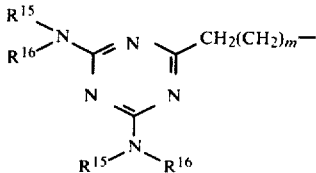   XVI wherein
m is as hereinbefore defined, $R^{15}$ and $R^{16}$, which may be the same or different, are each a hydrogen atom or a group of formula —$CH_2NR^{17}R^{18}$, either $R^{17}$ represents a hydrogen atom or a straight chain or branched alkyl group of 1 to 4 carbon atoms and $R^{18}$ represents such an alkyl group (which may be the same or different), or $R^{17}$ and $R^{18}$ conjointly, together with the nitrogen atom to which they are attached, denote a monovalent, mononuclear, heterocyclic radical of up to 8 carbon atoms, $R^{15}$ and $R^{16}$ being selected such that the compound of formula XV has at least two groups of formula —$CH_2NR^{17}R^{18}$, this reaction being effected by heating the reactants together, either alone or in a solvent such as xylene, methanol, ethanol, dioxan, acetone, glacial acetic acid, benzene, toluene, or pyridine, with elimination of the amine of formula $$R^{17}-NH-R^{18} \qquad \text{XVII}$$

Usually the reactants are heated at a temperature within the range 100° to 200° C.

The aminotriazines of formula XV used as starting materials may be prepared by a Mannich reaction between an aminotriazine of formula XII, formaldehyde, and a primary or secondary amine of formula XVII or a salt of such an amine. The nature of the amine used is not, in general, critical, but for economy, prevention of unwanted by-products, and ease of elimination during the reaction with the mercaptocarboxylic acid, it is preferred that $R^{17}$ represents a hydrogen atom and $R^{18}$ represents a methyl or ethyl group, or $R^{17}$ and $R^{18}$ both represent a methyl group or an ethyl group, or $R^{17}$ and $R^{18}$ together represent a group of formula —$(CH_2)_5$— or a group of formula —$(CH_2)_2O(CH_2)_2$—. As stated above, the acids and partial esters of this invention are useful as curing agents for epoxide resins.

Further aspects of this invention accordingly comprise curable compositions containing an epoxide resin and an aminotriazinepolycarboxylic acid or partial ester of formula I, and a process for curing an epoxide resin which comprises preparing and heating such a composition. An effective, i.e., a curing amount of the polycarboxylic acid or ester is used. The proportion of acid or partial ester to the epoxide resin will depend upon the particular acid or partial ester used and the properties sought in the curable composition and its cured product. The optimum proportion can readily be determined by methods familiar to those skilled in the art. By way of illustration, however, there is normally used sufficient of the polycarboxylic acid or partial ester to provide from 0.8 to 1.2 carboxylic groups per epoxide group of the epoxide resin.

Epoxide resins which may be employed in these compositions are preferably those containing groups of formula

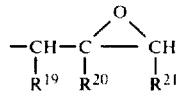  XVIII directly attached to atoms of oxygen, nitrogen, or sulfur, where either $R^{19}$ and $R^{21}$ each represent a hydrogen atom, iin which case $R^{20}$ denotes a hydrogen atom or a methyl group, or $R^{19}$ and $R^{21}$ together represent —$CH_2CH_2$—, in which case $R^{20}$ denotes a hydrogen atom.

As examples of such resins may be mentioned polyglycidyl and poly($\beta$-methylglycidyl) esters obtainable by reaction of a compound containing two or more carboxylic acid groups per molecule with epichlorohydrin, glycerol dichlorohydrin, or $\beta$-methylepichlorohydrin in the presence of an alkali. Such polyglycidyl esters may be derived from aliphatic polycarboxylic acids, e.g., oxalic acid, succinic acid, glutaric acid, adipic acid, pimelic acid, suberic acid, azelaic acid, sebacic acid, or dimerised or trimerised linoleic acid; from cycloaliphatic polycarboxylic acids such as tetrahydrophthalic acid, 4-methyltetrahydrophthalic acid, hexahydrophthalic acid, and 4-methylhexahydrophthalic acid; and from aromatic polycarboxylic acids such as phthalic acid, isophthalic acid, and terephthalic acid.

Further examples are polyglycidyl and poly($\beta$-methylglycidyl) ethers obtainable by reaction of a compound containing at least two free alcoholic hydroxyl and/or phenolic hydroxyl groups per molecule with the appropriate epichlorohydrin under alkaline conditions or, alternatively, in the presence of an acidic catalyst and subsequent treatment with alkali. These ethers may be made from acyclic alcohols such as ethylene glycol, diethylene glycol, and higher poly(oxyethylene) glycols, propane-1,2-diol and poly(oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylolpropane, pentaerythritol, sorbitol, and poly(epichlorohydrin); from cycloaliphatic alcohols such as resorcitol, quinitol, bis(4-hydroxycyclohexyl)methane, 2,2-bis(4-hydroxycyclohexyl)propane, and 1,1-bis(hydroxymethyl)cyclohex-3-ene; and from alcohols having aromatic nuclei, such as N,N-bis(2-hydroxyethyl)aniline and p,p'-bis(2-hydroxyethylamino)diphenylmethane. Or they may be made from mononuclear phenols, such as resorcinol and hydroquinone, and from polynuclear phenols, such as bis(4-hydroxyphenyl)methane, 4,4'-dihydroxydiphenyl, bis(4-hydroxyphenyl) sulfone, 1,1,2,2-tetrakis(4-hydroxyphenyl)ethane, 2,2-bis(4-hydroxyphenyl)propane (otherwise known as bisphenol A), 2,2-bis(3,5-dibromo-4-hydroxyphenyl)propane, and novolaks formed from aldehydes such as formaldehyde, acetaldehyde, chloral, and furfuraldehyde, with phenols such as phenol itself, and phenol substituted in the ring by chlorine atoms or by alkyl groups each containing up to nine carbon atoms, such as 4-chlorophenol, 2-methylphenol, and 4-tert.butylphenol.

Poly(N-glycidyl) compounds include, for example, those obtained by dehydrochlorination of the reaction products of epichlorohydrin with amines containing at least two amino-hydrogen atoms, such as aniline, n-butylamine, bis(4-aminophenyl)methane, and bis(4-methylaminophenyl)methane; triglycidyl isocyanurate; and N,N'-diglycidyl derivatives of cyclic alkylene ureas, such as ethyleneurea and 1,3-propyleneurea, and of hydantoins such as 5,5-dimethylhydantoin.

Examples of poly(S-glycidyl) compounds are di-S-glycidyl derivatives of dithiols such as ethane-1,2-dithiol and bis(4-mercaptomethylphenyl) ether.

Examples of epoxide resins having groups of formula XVIII where $R^{19}$ and $R^{21}$ conjointly denote a —$CH_2CH_2$— group are bis(2,3-epoxycyclopentyl) ether, 2,3-epoxycyclopentyl glydicyl ether, and 1,2-bis(2,3-epoxycyclopentyloxy)ethane.

Epoxide resins having the 1,2-epoxide groups attached to different kinds of hetero atoms may be employed, e.g., the N,N,O-triglycidyl derivatives of 4-aminophenol, and glycidyl etherglycidyl ether of salicylic acid, N-glycidyl-N'-(2-glycidyloxypropyl)-5,5-dimethylhydantoin, and 2-glycidyloxy-1,3-bis(5,5-dimethyl-1-glycidylhydantoin-3-yl)propane.

Epoxide resins in which some or all of the epoxide groups are not terminal may also be employed, such as vinylcyclohexene dioxide, limonene dioxide, dicyclopentadiene dioxide, 4-oxatetracyclo[6,2.1.0$^{2,7}$.0$^{3,5}$]undec-9-yl glycidyl ether, 1,2-bis(4-oxatetracyclo[6.2.1.0$^{2,7}$.0$^{3,5}$]undec-9-yloxy)ethane, 3,4-epoxycyclohexylmethyl 3',4'-epoxycyclohexanecarboxylate and its 6,6'-dimethyl derivative, ethylene glycol bis(3,4-epoxycyclohexanecarboxylate), bis(3,4-epoxy-6-methylcyclohexyl) adipate, 3-(3,4-epoxycyclohexyl)-8,9-epoxy-2,4-dioxaspiro[5,5]undecane, and epoxidised butadiene or copolymers of butadiene with ethylenic compounds, e.g., styrene and acrylonitrile.

If desired, a mixture of epoxide resins may be used. Preferred epoxide resins are polyglycidyl ethers, polyglycidyl esters, and N,N'-diglycidylhydantoins, particularly those having a 1,2-epoxide content of more than 0.5 equivalent per kilogram. Specific preferred resins are N,N'-diglycidyl-5,5-dimethylhydantoin, polyglycidyl ethers of 2,2-bis(4-hydroxyphenyl)propane, of bis(4-hydroxyphenyl)methane, or of novolaks formed from formaldehyde and phenol, or phenol substituted in the ring by one chlorine atom or by one alkyl hydrocarbon group containing from one to nine carbon atoms.

The new compositions may further contain suitable accelerators, such as tertiary amines and quaternary ammonium salts, especially imidazole, dimethylaminoethanol, pyridine, and tetrabutylammonium iodide, or metal octanoates, particularly zinc octanoate or stannous octanoate. The compositions may further contain plasticisers, such as dibutyl phthalate and dioctyl phthalate, inert diluents such as tars and bitumen and so-called reactive diluents, especially monoepoxides such as n-butyl glycidyl ether, iso-octyl glycidyl ether, phenyl glycidyl ether, cresyl glycidyl ethers, glycidyl esters of tertiary, aliphatic monocarboxylic acids, glycidyl acrylate, and glycidyl methacrylate. They may also contain additives such as fillers, reinforcing materials, coloring matter, flow control agents, flame inhibitors, and mold lubricants. Suitable extenders, fillers, and reinforcing materials are, for example, glass fibers, carbon fibers, ballotini, mica, quartz flour, calcium carbonate, cellulose, kaolin, wollastonite, colloidal silica having a large specific surface area, powdered poly(vinyl chloride), and powdered polyolefin hydrocarbons such as polyethylene and polypropylene.

The curable compositions of this invention may be used as laminating resins, sinter powders, impregnating and casting resins, molding compositions, putties and sealing compounds, potting and insulating compounds for the electrical industry, and adhesives, and also in the manufacture of such products, and are particularly suitable for use as coatings, both as paints and lacquers and as powder coatings.

The following Examples illustrate the invention. Unless otherwise specified, parts are by weight.

Epoxide Resin I denotes a diglycidyl ether of bisphenol A, advanced with bisphenol A to an epoxide content of 1.3 equiv./kg.

Epoxide Resin II denotes a diglycidyl ether of bisphenol A, having an epoxide content of 5.23 equiv./kg.

Epoxide Resin III denotes a diglycidyl ether of bisphenol A, having an epoxide content of 5.1 equiv./kg.

Epoxide Resin IV denotes N,N'-diglycidyl-5,5-dimethylhydantoin.

Epoxide Resin V denotes a diglycidyl ether similar to Epoxide Resin I but advanced to an epoxide content of 1.0 equiv./kg.

EXAMPLE 1

3-Mercaptopropionic acid (99% pure, 322 g; 3 moles) was weighed into a 1 liter glass flask fitted with a stirrer, thermometer, and reflux condenser. The flask was heated until the contents reached 95° C. and then melamine (63 g; 0.5 mole) was added. The temperature was adjusted to 90° C., at which temperature the contents were liquid but still contained some undissolved melamine. Over a period of 4 minutes there was added an aqueous solution of 36.5% w/w formaldehyde stabilised with 6% methanol (246 g; 3 moles). The mixture became clear and an exothermic reaction commenced. The temperature was kept at 100° C., then the mixture was cooled to a white paste.

The paste was mixed with an equal weight of water and with the same weight of ethanol. It was heated to 56° C., giving a clear solution. On cooling, this solution deposited crystals. After being allowed to stand overnight the crystals were filtered off and recrystallised from 50% aqueous ethanol. The crystals were dried in a vacuum oven at 70° C. to give hexakis(N-2-carboxyethylthiomethyl)melamine, melting at 153°–154° C.

Elemental analysis gave the following results:

| Calculated for $C_{27}H_{42}N_6O_{12}S_6$ | Found |
|---|---|
| C 38.84% | 38.6% |
| H 5.07% | 5.0% |
| N 10.06% | 10.1% |
| O 22.99% | 23.0% |
| S 23.04% | 23.0% |

The acid value of this material was found to be 7.38 equiv./kg, the theoretical value being 7.19 equiv./kg.

EXAMPLE 2

Example 1 was repeated, but at the end of the reaction volatile material was removed by distillation, first at atmospheric pressure, then under vacuum, the mixture being heated finally to 140° C./64 mm Hg. The product was cooled to 110° C., poured into a flat dish, and the clear colorless, viscous liquid was allowed to cool. The product, crude hexakis(N-2-carboxyethylthiomethyl)melamine (421 g; 100% yield), was stored at 25°–35° C. for 11 days and became a hard, white, translucent mass which could be ground to a powder. This powder had an acid value of 7.34 equiv./kg (theoretical value 7.19 equiv./kg) and melted at 134°–138° C. A sample was recrystallised from 50% aqueous ethanol: its melting point was then 148°–152° C.

EXAMPLE 3

A liquid, methylated melamine-formaldehyde resin (287.5 g; non-volatile content 97% melamine:formaldehyde:methyl molar ratio = 1:6:4.5) was added to thioglycolic acid (332.2 g; 98.9% pure) at 100° C. Addition took 30 minutes, the temperature being kept at 90°–110° C. The mixture was then heated at 120° C. to distil out volatile materials, the distillation being completed at 128° C. under a water pump vacuum. The distillate, which weighed 109 g, comprised methanol from the reaction between thioglycolic acid and the methylated resin, volatile material from the methylated resin itself, and water, methanol, and dimethoxymethane from the condensation together of two or more melamine rings.

The distillation residue was poured, whilst still hot, onto a flat tray and allowed to cool. This material was a clear, hard, colorless, resinous solid which softened at 62° C. Gel permeation chromatography confirmed that a considerable increase in molecular weight had occurred as a result of the reaction; while the starting material was predominantly composed of mononuclear species, a large proportion of the product had a molecular weight approaching 2,000, as shown by exceeding the exclusion limit of the column, thus providing further evidence that two or more melamine rings had linked together.

The acid value of this material was 4.73 equiv./kg.; the calculated value, based on the amount of thioglycolic acid used, is 7.0 equiv./kg. It is believed that the low acid value was a consequence of the further reaction of the carboxyl groups in the etherified product with some of the liberated methanol to give the corresponding methyl esters. This belief was substantiated by saponification of the product with standard sodium hydroxide solution, the neutralisation value being greatly increased. No evidence was found for esterification of liberated methanol with as yet unreacted thioglycolic acid.

Further confirmatory evidence for the formation of the esters was found by examination of the $^{13}C$ NMR spectrum, which showed two new peaks, neither of which is present in the spectra of the melamine resin starting material, thioglycolic acid, or the product of Example 7 (see below):

| $^{13}$C-NMR shifts (ppm) due to carbonyl carbon | | |
| --- | --- | --- |
| | COOH | COOCH$_3$ |
| thioglycolic acid | 172.0 | none |
| product of Example 7 | 171.41 | none |
| product of Example 3 | 171.48 | 170.61 |

| $^{13}$C-NMR shifts (ppm) due to methyl carbon | | |
| --- | --- | --- |
| | CH$_2$OCH$_3$ | COOCH$_3$ |
| melamine resin starting material | 55.02 | none |
| product of Example 3 | none | 52.2 |

The shifts of the new peaks due to the presence of methyl ester are underlined.

EXAMPLE 4

"Cymel" 1156 (74.1 g, 0.14 mole; a highly n-butylated hexamethylolmelamine supplied by American Cyanamid Corporation, having a Gardner-Holdt viscosity at 25° C. of Z$_2$-Z$_4$, a nitrogen content of 16.7%, and a solids content of 98%; "Cymel" is a trade mark), and 3-mercaptopropionic acid (45.9 g, 0.42 mole) were heated in a conical flask on a hotplate fitted with a magnetic stirrer. The mixture was heated at 70° C. for 40 minutes, then at 110° C. for 5 minutes. The thiol value of the product was less than 0.01 mole/kg, corresponding to over 99.7% reaction of the thiol group content originally present. The acid value of this product was 3.21 equiv./kg; the calculated value for a tris(N-2-carboxyethylthiomethyl)tris(N-n-butoxymethyl)melamine dissolved in the liberated n-butanol of reaction is 3.60 equiv./kg. The low acid value found is caused by partial esterification.

EXAMPLE 5

The method of Example 4 was repeated, using 78.1 g (0.15 mole) of "Cymel" 1156 and 41.9 g (0.44 mole) of freshly distilled thioglycolic acid. The thiol value of the product indicated over 99% reaction and the product had an acid value of 3.01 equiv./kg; the calculated value for a tris(N-carboxymethylthiomethyl)tris(N-n-butoxymethyl)melamine dissolved in the liberated n-butanol of reaction is 3.80 equiv./kg. The low acid value found is caused by partial esterification.

EXAMPLE 6

"Cymel" 1156 (76.0 g, 0.145 mole) and thiomalic acid (44.0 g, 0.29 mole) were heated with stirring at 75°-85° C. for 40 minutes, at the end of which time the thiol value indicated over 99% reaction. Xylene (23.4 g) was added to give a clear, viscous, very pale brown solution. The acid value of the product was 3.68 equiv./kg (expressed as the value before dilution with xylene): the calculated value for a bis(N-1,2-(dicarboxy)ethylthiomethyl)tetrakis(N-n-butoxymethyl)melamine dissolved in the liberated n-butanol of reaction is 4.09 equiv./kg. The low acid value found is caused by partial esterification.

EXAMPLE 7

Thioglycolic acid (282 g; 97.9% pure; 3 moles) was mixed with melamine (64 g; 0.5 mole) and water (200 ml) to give a uniform viscous suspension. Formaldehyde solution (36.3% in water; 246 g; 3 moles) was added and the mixture was heated to 65° C., when it clarified. The mixture was then heated under reflux for 30 minutes and distilled at atmospheric pressure. When 323 g of distillation had been collected, and the flask contents had reached 110° C., the distillation was stopped and the residue was cooled to give 441 g of a clear viscous liquid. The content of non-volatile material in this product was found, by heating 1 g at 120° C. for 1 hour, to be 87.0%. The acid value of this product, expressed in terms of non-volatile content, was 7.68 equiv./kg. The calculated value for hexakis(N-carboxymethylthiomethyl)melamine is 7.99 equiv./kg.

EXAMPLE 8

Melamine (32 g; 0.25 mole), 3-mercaptopropionic acid (98.5% pure; 80.7 g; 0.75 mole), and distilled water (150 ml) were heated and stirred together. At 93° C. a clear solution was formed of the melamine salt of 3-mercaptopropionic acid. To this, at 100° C., was slowly added 36.6% aqueous formaldehyde solution 61.5 g; 0.75 mole). Addition took 7 minutes, the temperature being kept at 85°-90° C. without external heating due to the exothermic nature of the reaction. The solution became cloudy and after stirring for a further 6 minutes there was no detectable odour of formaldehyde. Stirring was then stopped and the mixture was allowed to cool. The upper layer was then poured from a whitish, tacky lower layer, which was cooled further, crushed, filtered off, and washed with ice-cold water. The solid was dried in a vacuum oven at 40° C. to give sym. and/or asym. tris(N-2-carboxyethylthiomethyl)melamine, 114 g (93.7% theory), a white powder melting at 166° to 175° C., acid value 6.01 equiv./kg (theoretical value 6.24 equiv./kg). This product had no detectable thiol content.

EXAMPLE 9

Acetoguanamine (6.25 g; 0.05 mole) and 3-mercaptopropionic acid (21.23 g; 0.20 mole) were stirred together and heated. When the mixture reached 85° C. it cleared, and at 95° C. 36.0% aqueous formaldehyde (16.67 g; 0.20 mole) was added, followed by distilled water (20 ml). The mixture was heated to 100° C., and a white precipitate formed. After being heated at 100° C. for a further 20 minutes the mixture was cooled to ambient temperature, filtered, and the precipitate was washed with cold water. The yield, after drying in a vacuum oven, was 18.7 g (62.6% theory); the product melted at 220°-227° C. The acid value of this product was 6.64 equiv./kg. the theoretical value for tetrakis(N-2-carboxyethylthiomethyl)acetoguanamine being 6.69 equiv./kg.

EXAMPLE 10

Benzoguanamine (9.35 g; 0.05 mole) and 3-mercaptopropionic acid (21.23 g; 0.20 mole) were stirred together and heated. At 96° C. the mixture became clear and 36.0% aqueous formaldehyde (16.67 g; 0.20 mole) was added. The temperature was maintained at 82°-89° C. for 20 minutes, then cooling was applied. An oil separated which, on further stirring, solidified. Distilled water (100 ml) was added, and the white solid was filtered off and dried in a vacuum oven. The yield of crude material was 28.8 g (87.3% of theory); it melted at 110°-118° C. The acid value of the material was 6.30 equiv./kg, the theoretical value for tetrakis(N-2-carboxyethylthiomethyl)benzoguanamine being 6.06 equiv./kg.

EXAMPLE 11

"Cymel" 1156 (38.8 g), 2-ethylhexyl thioglycolate (40.8 g), and 3-mercaptopropionic acid (21.2 g) were mixed in a flask. The molar ratio of these components is 1:2.63:2.63. The flask was attached to a rotary evaporator and heated in a water bath at 95° C. for 9½ hours. Vacuum was applied and a distillate (16.9 g) was collected over 2 hours. The product remaining in the flask (82.6 g) had a thiol value of 0.22 equiv./kg, indicating over 95% reaction. It was a colorless, easily pourable, faintly turbid liquid having an acid value of 2.35 equiv./kg. The calculated acid value of a tris(N-2-carboxyethylthiomethyl)tris(N-2-(ethyl)hexyloxycarbonylmethylthiomethyl)melamine is 2.66 equiv./kg.

EXAMPLE 12

Benzoguanamine (9.35 g; 0.05 mole), 3-mercaptopropionic acid (21.23 g; 0.20 mole), and n-butyraldehyde (14.42 g; 0.20 mole) were heated and stirred to 64° C., at which temperature the reaction became exothermic. After 30 minutes at 50°-60° C. the mixture was a clear liquid, with traces of a suspended solid. It was cooled to room temperature, giving a viscous pasty mass.

The product was suspended in cold acetone (50 ml) and filtered. The residue was washed twice with 25 ml of cold acetone and dried to give 13.7 g of a white powder, melting point 142°-148° C. This product had an acid value of 4.1 equiv./kg, indicating that, on average, 3.4 hydrogen atoms attached to nitrogen in the benzoguanamine molecule had been replaced by groups of formula

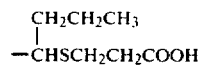

XIX

EXAMPLE 13

Melamine (31.6 g; 0.25 mole), 3-mercaptopropionic acid (79.6 g; 0.75 mole), and distilled water (150 g) were heated: when the mixture reached 83° C. it formed a clear liquid. It was then cooled to 75° C. and n-butyraldehyde (54.0 g; 0.75 mole) was added slowly, keeping the temperature between 70° and 80° C. On complete addition the mixture was heated under reflux for 4½ hours.

The mixture was cooled and a clear aqueous layer was removed. The organic layer was washed with distilled water (2×250 ml) and then dissolved in 10% sodium carbonate solution (500 ml). The solution was neutralised with acetic acid solution (10%), which precipitated the product. This was filtered off and dried to give 106.5 g of a white solid, sym and/or asym. tris(N-1-(2-carboxyethylthio)butyl)melamine, having an acid value of 4.40 equiv./kg. The calculated acid value of a tris(N-1-(2-carboxyethylthio)butyl)melamine is 4.54 equiv./kg. The $^{13}$C NMR spectrum of the product was consistent with such a compound.

EXAMPLE 14

Lauroguanamine (53.1 g, 0.2 mol), 3-mercaptopropionic acid (84.9 g, 0.8 mol), and 50 g of water were heated to 85° C., the mixture forming two liquid phases. Then 65.8 g (0.8 mol) of a 36.5% aqueous solution of formaldehyde was added dropwise. After about 15 g had been added the reaction mixture became a clear yellow solution. The addition of the formaldehyde was completed over four minutes, the temperature of the reaction mixture rising to 93° C. The mixture was heated to reflux (98°-100° C.) for 30 minutes, during which time a white solid precipitated. After being cooled, the mixture was filtered and the white solid was washed several times with hot water. The yield of the product, after being dried in vacuo was 109 g. The product, substantially tetrakis(N-2-carboxyethylthiomethyl)lauroguanamine, had an acid value of 4.38 equiv./kg, a negligibly low thiol value, and melted at 155° C. (determined on a Kofler bench).

EXAMPLE 15

Recrystallised hexakis(N-2-carboxyethylthiomethyl)-melamine, prepared as described in Example 2 (8.34 g, 0.01 mol), and 2.95 g (0.025 mol) of 2-n-butoxyethanol were heated at 150° C. Initially, a thick, white paste was formed which was barely stirrable, but after 40 minutes it changed into a thin, clear, colorless solution. Heating at 150° C. was continued for a further 100 minutes, then the mixture was cooled. The product, a clear, colorless liquid with a sweetish smell, had an acid value of 3.48 equiv./kg (calculated initial value of the mixture, 5.49 equiv./kg; calculated value for a product containing on average 2.5 2-(n-butoxyethoxycarbonyl)ethylthiomethyl groups per molecule is 3.80 equiv./kg), and a solids content (determined by heating a 0.5 g sample for 60 minutes at 120° C.) of 92.4% (calculated initial value, 73.9%).

EXAMPLE 16

A composition was prepared containing the following:

| | |
|---|---|
| 60% Solution in EEA[a] of Epoxide resin I | 200 g |
| 50% Solution in EEA of Product of Example 2 | 44 g |
| 10% Solution in EEA of poly(butyl acrylate)[b] | 7.5 g |

[a] EEA denotes 2-ethoxyethyl acetate
[b] added as flow control agent

A further quantity of 2-ethoxyethyl acetate was added in order to reduce the viscosity of the mixture to about 80 mPa s. Steel plates were spray-coated with this solution and baked for 15 minutes at 200° C.

The following observations and tests were made on the coatings:

TABLE I

| | |
|---|---|
| Appearance | clear, smooth yellow films |
| Thickness | 15-25 μm |
| Acetone resistance (contact with cotton wool swab soaked in acetone for 1 minute) | very slight effect |
| Reverse impact[c] | pass |
| Extensibility (DIN 53156) | 9.5 mm |

[c] The reverse impact test comprised dropping a pointed 2 kg weight, maximum diameter of area of impact 2 cm, from a height of 80 cm onto the reverse side of the coated plate.

A 'pass' result indicates that the coating was not broken. These results indicate that the coatings are cross-linked and have very good mechanical properties.

EXAMPLE 17

Portions of each of the products of Examples 4, 5, and 6 were separately mixed with a stoichiometric amount of Epoxide Resin II and diluted with 2-n-butoxyethanol. The formulations were as shown in the following Table:

TABLE II

| | Composition (parts) | | |
|---|---|---|---|
| | A | B | C |
| Product of Example 4 | 244 | — | — |
| Product of Example 5 | — | 261 | — |
| Product of Example 6 | — | — | 213 |
| Epoxide Resin II | 150 | 150 | 150 |
| 2-n-Butoxyethanol | 40 | 30 | 80 |

Films, approximately 100 μm thick, were cast from these compositions onto glass plates, dried at room temperature for 1 hour, then baked for ½ hour as indicated below. The results are as given in the following Table:

TABLE III

| Composition | Cure Temp. | Appearance | EMK resistance[d] | Hardness[e] |
|---|---|---|---|---|
| A | 120° C. | Clear, colorless, glossy | Unaffected | Unaffected |
| B | 120° C. | Clear, colorless, glossy | Unaffected | Unaffected |
| C | 140° C. | Clear, slightly yellow, glossy | Unaffected | Unaffected |

[d] EMK resistance was determined by giving the coating 20 double rubs with a cotton wool swab soaked in ethyl methyl ketone
[e] Hardness was assessed by attempting to scratch the film with a finger nail

EXAMPLE 18

The product from Example 7 (5.0 g) was mixed with Epoxide Resin III (6.8 g) and diluted with 2-ethoxyethanol (5 ml) to give a clear solution. A film of this solution was cast onto a glass plate and baked for 30 minutes at 100° C., giving a tough, hard film, unaffected by 10 rubs with a cotton wool swab soaked in acetone.

EXAMPLE 19

Samples weighing 1.0 g of the products of Examples 8, 9, and 10 were dissolved in dimethylaminoethanol (DMAE) and water or in dimethylformamide (DMF) and blended with Epoxide Resin IV or with Epoxide Resin II described above. The mixtures were coated onto glass plates, at a thickness of 100 μm, and baked in an oven at 150° C. for 30 minutes. They were then given 20 double rubs with a cotton wool swab soaked in ethyl methyl ketone. The results were as shown in the following Table:

TABLE IV

| Product of Example | DMAE (g) | Water (g) | DMF (g) | Epoxide type | Resin quantity (g) | Appearance after baking | EMK resistance |
|---|---|---|---|---|---|---|---|
| 8 | 0.65 | 1.27 | — | IV | 2.92 | hard, orange-yellow | slight softening |
| 9 | 0.76 | 1.19 | — | IV | 2.95 | hard, yellow-brown | unaffected |
| 10 | — | — | 2.19 | II | 1.19 | hard, clear, glossy | unaffected |

EXAMPLE 20

The product of Example 11 (1 g) was mixed with 4.3 g of a 60% solution of Epoxide Resin V in 2-n-butoxyethanol and diluted with 2-ethoxyethanol (1 g).

A film of wet thickness 75 μm was cast onto a glass plate and then heated at 150° C. for 30 minutes. The film was then found to be clear, hard, and tough. It was unaffected when rubbed 20 times with cotton wool soaked in xylene, and underwent only slight softening when rubbed 20 times with cotton wool soaked in 2-ethoxyethanol.

EXAMPLE 21

The partial ester produced in Example 15 (1 g) was mixed with 5.87 g of a 60% solution of Epoxide Resin V in 2-n-butoxyethanol, and spread in a layer 75 μm thick on a glass plate. It was cured at 150° C. for 30 minutes, forming a clear, colorless, glossy, tough, flexible film which was unaffected by rubbing 20 times with a cotton wool swab soaked in 2-n-butoxyethanol.

What is claimed is:

1. A compound of the formula

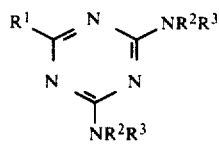

where
R$^1$ represents a group of formula —NR$^2$R$^3$, a straight chain or branched alkyl group of from 1 to 17 carbon atoms, a mononuclear aryl group of 6 to 10 carbon atoms, a phenylalkylene group wherein the alkylene moiety has from 1 to 4 carbon atoms, or a group of formula

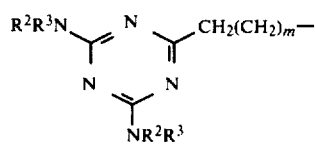

R$^2$ and R$^3$ may be the same or different and each represents a hydrogen atom, a group of formula —CHR$^4$OR$^5$, a group of formula

—CHR$^4$—S—R$^6$—COOQ    IIA or a group of formula

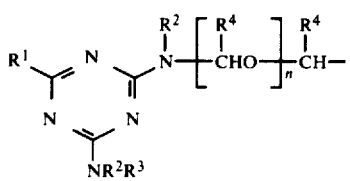

R$^2$ and R$^3$ in formulae I and III being selected such that at most one of them represents a group of formula III and at least two of them each represent a group of formula IIA;
m represents an integer of from 1 to 3;
each R$^4$ represents a hydrogen atom or a straight chain or branched alkyl group of from 1 to 3 carbon atoms;
each R$^5$ represents a hydrogen atom or a straight chain or branched alkyl group of from 1 to 8 carbon atoms;
each R$^6$ represents a divalent straight chain or branched alkylene group of from 1 to 4 carbon atoms, or a divalent straight chain or branched alkylene group of from 1 to 4 carbon atoms which is substituted by a group of formula

—COOQ    IIB;

each Q represents a hydrogen atom or a straight chain or branched alkyl group of from 1 to 8 carbon atoms, such that at least two Q in the formulae IIA and IIB each represent a hydrogen atom; and n represents zero or 1.

2. An acid according to claim 1, having a molecular weight of at most 2000.

3. An acid according to claim 1, wherein R$^1$ represents a methyl, phenyl, or undecyl group.

4. An acid according to claim 1, wherein all the R$^4$ each represent a hydrogen atom.

5. An acid according to claim 1, wherein at least one of the symbols R$^5$ represents a methyl, n-butyl, isobutyl, or 2-ethylhexyl group.

6. An acid according to claim 1, wherein all the R$^6$ each represent a methylene, ethylene, ethylidene, or 2-carboxyethylidene group.

7. An acid according to claim 1, which is also of the formula

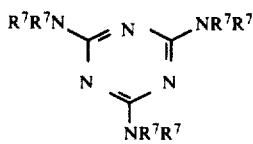

where from two to six of R$^7$ each is a group of formula —CH$_2$SCH$_2$COOQ, —CH$_2$SCH$_2$CH$_2$COOQ, —CH$_2$SCH(COOQ)CH$_2$COOQ, or —CH$_2$SCH(CH$_3$)COOQ, where each Q represents a hydrogen atom or a straight chain or branched alkyl group of from 1 to 8 carbon atoms, such that at least two Q each represent a hydrogen atom, the remaining R$^7$, if any, each being a hydrogen atom.

8. An acid according to claim 1, which is also of the formula

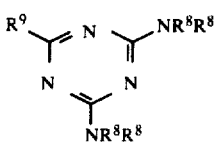

where
from two to four of R$^8$ each is a group of formula —CH$_2$SCH$_2$COOQ, —CH$_2$SCH$_2$CH$_2$COOQ, —CH$_2$SCH(COOQ)CH$_2$COOQ, or —CH$_2$SCH(CH$_3$)COOQ, where each Q represents a hydrogen atom or a straight chain or branched alkyl group of from 1 to 8 carbon atoms, such that at least two Q each represent a hydrogen atom, the remaining R$^8$, if any, each being a hydrogen atom, and
R$^9$ is a methyl, phenyl, or undecyl group.

9. An acid according to claim 1, which is hexakis(N-2-carboxyethylthiomethyl)melamine, hexakis(N-carboxymethylthiomethyl)melamine, tetrakis(N-2-carboxyethylthiomethyl)acetoguanamine, tetrakis(N-2-carboxyethylthiomethyl)benzoguanamine, or tetrakis(N-2-carboxyethylthiomethyl)lauroguanamine.

* * * * *